United States Patent [19]

Kisfaludy et al.

[11] 4,299,821
[45] Nov. 10, 1981

[54] TRIPEPTIDES ACTING ON THE CENTRAL NERVOUS SYSTEM AND A PROCESS FOR THE PREPARATION THEREOF

[75] Inventors: Lajos Kisfaludy; Támas Szirtes, both of Budapest; Lajos Baláspiri, Szeged; Éva Pálosi, Budapest; László Szporny, Budapest; Adám Sarkadi, Budapest, all of Hungary

[73] Assignee: Richter Gedeon Végyeszeti Gyár Rt., Budapest, Hungary

[21] Appl. No.: 163,829

[22] Filed: Jun. 27, 1980

[30] Foreign Application Priority Data

Jun. 28, 1979 [HU] Hungary .............................. RI 717

[51] Int. Cl.³ ...................... A61K 37/00; C07C 103/52
[52] U.S. Cl. .............................. 424/177; 260/112.5 R; 260/112.5 TR
[58] Field of Search ............... 260/112.5 TR; 424/177

[56] References Cited

U.S. PATENT DOCUMENTS 3,959,248  5/1976  Veber et al. .............. 260/112.5 TR

OTHER PUBLICATIONS

C. Oliver et al., Biochem. and Biophys. Res. Commun., vol. 84, (1978) 1097-1102.
G. R. Pettit, "Synthetic Peptides" vol. 4, pp. 170, 171; vol. 3, pp. 172-173.
Chem. Abstr. vol. 86, (1977) 55688.

*Primary Examiner*—Delbert R. Phillips
*Attorney, Agent, or Firm*—Keil & Witherspoon

[57] ABSTRACT

The invention relates to new peptide derivatives which act on the central nervous system and correspond to the general formula (I), $$Glp-X-Y-NH-A \qquad (I)$$

wherein
X is L-norleucyl, L-leucyl, L-norvalyl, D-leucyl, L-prolyl, L-2-aminobutyryl, L-valyl, L-threonyl, L-isoleucyl, L-2-aminodecanoyl, L-cyclohexylalanyl or L-tert.-butyl-seryl group and
Y is L-prolyl group, or
X is L-histidyl group and
Y is L-homoprolyl or D-pipecolyl group, furthermore
A is hydrogen, a $C_{1-10}$ alkyl group or a $C_{1-3}$ alkyl group having a dimethylamino substituent,
with the proviso that if X is L-leucyl group, A is other than hydrogen, and pharmaceutically acceptable complexes thereof.

These compounds are prepared by methods commonly applied in the peptide chemistry.

5 Claims, No Drawings

TRIPEPTIDES ACTING ON THE CENTRAL NERVOUS SYSTEM AND A PROCESS FOR THE PREPARATION THEREOF

The invention relates to new tripeptides which act on the central nervous system and pharmaceutical compositions containing the same, as well as to a process for the preparation thereof.

The new compounds according to the invention correspond to the general formula (I),

$$\text{Glp—X—Y—NH—A} \qquad (I)$$

wherein
- X is L-norleucyl, L-leucyl, L-norvalyl, D-leucyl, L-prolyl, L-2-aminobutyryl, L-valyl, L-threonyl, L-isoleucyl, L-2-aminodecanoyl, L-cyclohexylalanyl or L-tert.-butyl-seryl group and
- Y is L-prolyl group, or
- X is L-histidyl group and
- Y is L-homoprolyl or D-pipecolyl group, furthermore
- A is hydrogen, a $C_{1-10}$ alkyl group or a $C_{1-3}$ alkyl group having a dimethylamino substituent, with the proviso that if X is L-leucyl group, A is other than hydrogen.

The pharmaceutically acceptable complexes of these compounds also fall within the scope of the invention.

The new tripeptide derivatives of the general formula (I) are structural analogues of L-pyroglutamyl-L-histidyl-L-prolinamide (Glp-His-Pro-$NH_2$) also known as "thyrotropin-releasing hormone" (TRH), in which one of the amino acid groups, in particular the L-His group in position 2 or the L-Pro group in position 3, is replaced by another amino acid group defined above.

The existence of TRH was already known in the sixties, but its structure was elucidated only in 1969 by R. Guillemin et al., and independent researches conducted by A. Schally et al. in 1970 confirmed this structure (see C. Y. Bowers et al., Endocrinology 86, 1143 /1970/; R. Burgus et al., C. R. Acad. Sci. /Paris/ 269, 1870 /1969/).

The tripeptide TRH was described originally as a factor which regulates the liberation of thyrotropin (TSH) in the hypophysis of mammals. Subsequent research has revealed, however, that the biological function of this tripeptide is not restricted to the regulation of thyrotropin release, it acts on the central nervous system (CNS) as well, and this recognition opened a new field of investigations (see N. P. Plotnikoff et al., Science 178, 417 /1972/; A. J. Prange et al., Lancet 2, 999 /1972/). Thus, it was soon discovered that TRH, beside its horomonal function, considerably decreases the duration of sleeping caused by barbiturates and alcohol, suppresses the hypothermy provoked by various pharmaceuticals and increases the locomotive activity. An additional important factor of the CNS effects of TRH is the inhibition of catalepsy provoked by Haloperidol. There appeared a demand in the therapeutical practice for TRH analogues which exert only a weak effect on the hypophysis but act on the central nervous system to the same or even higher degree than TRH. The compounds listed in the published German patent application Nos. 2,343,035, 2,343,037, 2,449,167, 2,514,381, 2,609,154 and 2,639,393 and in the Belgian patent specification No. 819,198 were synthetized with this aim. This extensive research work, the results and experiences of which were reviewed by A. J. Prangle et al. ("The Role of Hormones in Depression", Life Sciences 20, 1305 /1977/) and A. V. Schally et al. ("Hypothalamic Regulatory Hormones", Ann. Rev. Biochem. 47, 89 /1978/) has not led, however, to results satisfying the demands of therapy in all respects.

Now it has been found that when replacing one of the amino acids of the tripeptide TRH by another amino acid new compounds are obtained which do not show the hormonal effect characteristic of TRH or have only minimum hormonal effects, whereas the CNS effects are retained or increased, sometimes to a considerable extent. In this respect the compounds in which a straight-chained or branched aliphatic amino acid group is substituted for His in position 2 are of particular importance. These TRH analogues are practically devoid of hormonal effects and at the same time they exert much stronger effects on the central nervous system than TRH. TRH analogues in which the L-histidyl group in position 2 is retained but the L-prolyl group in position 3 is replaced by a L-homoprolyl or D-pipecolyl group are also valuable substances.

The new tripeptide amides of the general formula (I) are prepared according to the invention from the respective amino acids or amino acid derivatives by conventional methods of the peptide chemistry. It is preferred to apply a substituted amino acid amide of the general formula Y-NH-A, wherein Y and A are as defined above, i.e. which contains the required third amino acid group of the end-product, as starting substance, and to couple this amide first with the L-amino acid corresponding to group X and then with the L-pyroglutamyl group which is the first amino acid group of the end-product. Any protecting group present in the molecule is split off after these coupling steps. If a tripeptide amide of the general formula (I), wherein X stands for L-histidyl group, is to be prepared, one can also proceed so that the starting substance of the general formula Y-NH-A is acylated directly with a protected azide prepared from the dipeptide hydrazide of the formula Z-Gln-HIs-NH-$NH_2$, wherein Z stands for benzyloxycarbonyl group, the Z protecting group of the resulting protected tripeptide amide of the general formula Z-Gln-His-Y-NH-A, wherein Y and A are as defined above, is split off, and the glutaminyl group of the resulting compound is cyclised into pyroglutamyl group by heat treatment. According to a preferred method the benzyloxycarbonyl group is split off by catalytic hydrogenation, thereafter the catalyst is filtered off, acetic acid is added to the filtrate, and the resulting mixture is heated to 60° to 70° C. to effect ring closure. This latter step requires about 30 minutes.

When the tripeptide molecule is built up stepwise, the starting substance of the general formula Y-NH-A, applied preferably in excess, is reacted with an activated derivative, particularly with the pentafluorophenyl ester, of a protected L-amino acid of the general formula BOC-X-OH, wherein BOC stands for tert.-butoxycarbonyl group. In this reaction the respective dipeptide derivative of the general formula BOC-X-Y-NH-A is cbtained in an extremely short time (some minutes). The reaction mixture can be processed very easily, and the resulting product is generally sufficiently pure for utilizng it directly in the next step.

The same dipeptide derivatives of the general formula BOC-X-Y-NH-A can also be prepared, however, by other coupling methods, such as utilizing a mixed anhydride of the respective protected L-amino acid.

The dipeptide derivative of the general formula BOC-X-Y-NH-A is subjected then to acidolysis to obtain the free dipeptide of the general formula H-X-Y-NH-A, and this latter compound is reacted preferably also with the pentafluorophenyl ester of the protected L-pyroglutamic acid of the formula Z-Glp-OH, to obtain the respective protected tripeptide derivative of the general formula Z-Glp-X-Y-NH-A. The Z protecting group of this compound is split off preferably by catalytic hydrogenation.

One can also apply, however, L-glutamic acid or a reactive derivative thereof as acylating agent. In this instance the pyroglutamine ring of the compound of the general formula (I) is formed in the last step of the synthesis, by subjecting the glutamine derivative to heat treatment as described above.

The method in which the starting substance of the general formula Y-NH-A is acylated with an azide prepared from the protected dipeptide hydrazide of the formula Z-Gln-His-NH-NH$_2$ has the advantage that this hydrazide intermediate is easy to crystallize, thus it can be isolated in very high purity.

The tripeptide amide derivatives of the general formula (I), prepared as described above, can be separated from the reaction mixture by crystallization or freeze-drying, and can be converted into their complexes by methods known per se. The end-products can be purified by simple recrystallization or reprecipitation; column chromatographic purification can also be applied, however, if necessary. In some instances it is preferred to remove first the by-products from the reaction mixture, whereafter the end-product can be isolated by freeze-drying with the required purity grade.

The pharmacological effects of the tripeptide derivatives of the general formula (I) were tested by the following biological methods:

(1) Inhibition of Haloperidol-induced catalepsy on rats (see J. Delay and P. Deniker: Compt. Rend. Congr. Med. Alenistes Neurologistes, 19, 497, Luxembourg, 1952)

The tests were performed on male Wistar rats weighing 160 to 180 g.

40 mg/kg of 4-(p-chlorophenyl)-1-(3-/p-fluorobenzoyl/propyl)-piperidin-4-ol (Haloperidol) were administered subcutaneously into the animals, and 120 minutes after this treatment the animals were checked for the appearance of catalepsy. The rats were divided into groups of 10 animals each, and treated intravenously with TRH or the new TRH analogues. The animals belonging to the control group received physiological saline. The catalepsy-suspending effects of the individual compounds were determined 15, 30, 60, 90 and 120 minutes after the treatment. The animals that had not changed their position for 30 seconds after placing their fore-paw onto a 7 cm high column were regarded as cataleptic.

The animals showing no sign of catalepsy were counted, and the ED$_{50}$ values of the compounds were calculated from these data by probit analysis.

(2) Potentiation of locomotive activity induced on mice by L-Dopa (see The Thyroid Axis, Drugs and Behavior, p. 116, A. J. Prage Jr., Raven Press, New York, 1974)

The tests were performed on groups of 15 male mice each, weighing 18 to 22 g.

First, the animals were treated intraperitoneally with 40 mg/kg of N-methyl-N-propargyl-benzylamine (Pargyline), and then an intraperitoneal dosage of 20 mg/kg of TRH or a TRH-analogue was introduced, followed by an intraperitoneal dosage of 100 mg/kg of L-Dopa. The locomotive activity of the animals was recorded 30, 60 and 90 minutes after this treatment, and the level of potentiation was expressed in percents related to the results observed with TRH. The data are listed in Table 1.

(3) Reserpine hypothermy-reversing effect on mice (see B. M. Askew: Life Sci. 2, 725–730 /1963/)

The tests were performed on groups of 10 male mice each, weighing 18 to 22 g. Reserpine was administered into the animals in an intraperitoneal dosage of 5 mg/kg, and 16 hours later the animals were treated with 20 mg/kg of TRH or a tripeptide under examination.

The rectal temperature of the animals was measured prior to the administration of reserpine (marked by "norm." in Table 1), 16 hours after the administration of reserpine (marked by "res." in Table 1), furthermore 1 and 2 hours after the administration of the tripeptide (marked by "obs. time" in Table 1). The data listed in Table 1 are the averages of the temperatures observed on the 10 animals.

(4) Influencing the duration of sleeping caused by hexobarbital

The tests were performed on groups of 10 male mice each. The animals were treated intravenously with 60 mg/kg of hexobarbital sodium (Evipan$^R$; Bayer), and 10 minutes later 20 mg/kg of TRH or a tripeptide under examination were administered intraperitoneally into the animals. The sleeping times of the animals were recorded, averages were calculated for the individual groups, and the results were expressed as percents related to the control group. The results are listed in Table 1.

(5) Ethanol narcosis (see J. M. Cott et al.: J. Pharm. Exp. Ther. 196, 594 /1976/)

The tests were performed on groups of 20 mice of both sexes, each weighing 18 to 22 g. 4.5 g of ethanol were introduced intraperitoneally into the animals, and 10 minutes later the animals were treated intraperitoneally with 20 mg/kg of TRH or a tripeptide under examination. The sleeping periods of the animals were recorded, averages were calculated for the individual groups, and the results were expressed as percents related to the control group. The results are listed in Table 1.

(6) Hormonal activity (TSH effect) on rats

The tests were performed on groups of 7 or 8 male Wistar rats each, weighing 200 g. The animals were treated intravenously with 20 mg/kg of TRH or a tripeptide under examination. The TSH reaction of the animals was evaluated 15 minutes after this treatment, by subjecting the blood plasma to radioimmune assay. The relative activities were calculated by the four-point method using a TPA 101 computer, and the activity of TRH was regarded as 100%.

The biological activity data of some of the compounds according to the invention, determined by the above tests, are listed in Table 1.

TABLE 1

| Glp—X—Y—NH—A | | | Inhibition of Haloperidol catalepsy | | Potentiation of the locomotive effect of L-Dopa | | | Reserpine hypothermy reversing effect Rectal temperature, °C. | | | | Decrease of sleeping period (% related to the control animals) | | TSH ef-fect |
|---|---|---|---|---|---|---|---|---|---|---|---|---|---|---|
| X | Y | A | ED₅₀ mg/kg | time min. | % after | | | norm. | res. | obs. time | | Hexobarb. | Ethanol | |
| | | | | | 30' | 60' | 90' | | | 1 h | 2 h | | | |
| Nva | Pro | H | 11.4 | 120 | 254 | 156 | 214 | 36.2 | 25.9 | 36.4 | 32.0 | 114 | 77 | 0 |
| Nleu | Pro | H | 16.8 | 120 | 249 | 105 | 112 | 36.3 | 27.1 | 37.6 | 32.2 | 77 | 74 | 3.8 |
| Leu | Pro | Et | 56.6 | 30 | 102 | 90 | 201 | 36.2 | 28.7 | 30.7 | 33.4 | 126 | 65 | 0 |
| His | HPro | H | 13.7 | 120 | 209 | 85 | 110 | 36.5 | 28.5 | 35.3 | 35.4 | 63 | 114 | 68.6 |
| Abu | Pro | H | 80 | 15 | 27 | 14 | 18 | 36.3 | 19.7 | 22.2 | 25.4 | 84 | 39 | 0.02 |
| TRH | | | 80 | 15 | 100 | 100 | 100 | 36.2 | 25.9 | 33.5 | 30.2 | 56 | 35 | 100.0 |

Duration of hexobarbital-induced sleeping: ($\bar{X} \pm SE$) = 38.4 ± 1.36 min.
Duration of ethanol-induced sleeping: ($\bar{X} \pm SE$) = 46.9 ± 2.17 min.

The data of Table 1 indicate that when His is replaced in the TRH molecule by a straight-chained or branched aliphatic amino acid residue, the hormonal effect disappears or is reduced considerably, whereas the effects exerted on the central nervous system increase, thus e.g. in the tests for inhibiting the Haloperidol-induced catalepsy a 2 to 7-fold increase can be observed. Some of the new TRH analogues also potentiate the locomotive activity and reduce the duration of sleeping provoked by hexobarbital or ethanol to a considerable extent. It is also worth noting that the His-containing new TRH analogues, which retain about 70% of the hormonal effect of the original molecule, exert simultaneously significant effects on the central nervous system.

The new tripeptide derivatives according to the invention as well as their pharmaceutically acceptable salts or complexes can be applied in the therapy in the form of conventional pharmaceutical compositions. These pharmaceutical compositions contain the active agents according to the invention in combination with mineral or organic carriers suitable for enteral or parenteral administration. The pharmaceutical compositions can be presented e.g. in the form of freeze-dried solids which may contain inert carbohydrates as carriers, furthermore as concentrated or diluted suspensions or emulsions, tablets, injectable preparations, etc. These compositions can be prepared by methods well known in the pharmaceutical industry.

The invention is elucidated in detail by the aid of the following non-limiting Examples. The abbreviations used in the examples are those commonly applied in the peptide chemistry (see J. Biol. Chem. 247, 977 /1972/). The additional abbreviations appearing in the examples have the following meanings:

Ada: L-2-aminodecanoic acid
Abu: L-2-aminobutyric acid
Cha: L-cyclohexylalanine
Pip- L-pipecolic acid
HPro: L-homoproline
DAE: 2-dimethylaminoethyl
DCC: dicyclohexyl carbodiimide
PFPOH: pentafluorophenol
DCU: dicyclohexyl urea
DMFA: dimethyl formamide The melting points given in the examples were determined on a Dr. Tottoli-type (Büchi) apparatus. The optical rotations were measured on a Perkin-Elmer 141 type polarimeter. When thin layer chromatography was used for identification or separation, chromatographic silica gel plates of "Kieselgel G nach Stahl" quality (E. Merck, Darmstadt) were applied as adsorbent, and the following solvent mixtures were utilized to develop the chromatograms:

(1) chloroform: methanol 9:1
(2) ethyl acetate: (pyridine:acetic acid:water 20:6:11) 9:1
(3) ethyl acetate: (pyridine:acetic acid:water 20:6:11) 8:2
(4) ethyl acetate: (pyridine:acetic acid:water 20:6:11) 3:2

The spots were developed with ninhydrin solution. The plates were dried at 105° C. for about 5 minutes after spraying, thereafter the chromatograms were exposed to chlorine gas, then, after aeration, treated with o-toludine-potassium iodide solution.

When column chromatography was applied to separate the substances, "Kieselgel G" grade silica gel (E. Merck) with a particle size of 0.062 to 0.2 mm was utilized as adsorbent.

The solutions were evaporated under reduced pressure in a "Rotavapor R" (Büchi) apparatus at temperatures not exceeding 50° C.

The pentafluorophenyl esters of the BOC-protected amino acids were prepared according to the method of L. Kisfaludy et al. (Ann. 1973, 1421).

EXAMPLE 1

L-Pyroglutamyl-L-norleucyl-L-prolinamide

Step 1: L-Norleucyl-L-prolinamide hydrochloride 2.28 g (20 mmoles) of H-Pro-NH₂ and 3.97 g (10 mmoles) of BOC-Nle-OPFP (L. Kisfaludy et al.: Hoppe-Sayler's Z. Physiol. Chemie 359, 887 /1978/) are dissolved in 40 ml of DMFA, and after 5 minutes of standing the solution is evaporated in vacuo. The oily residue is dissolved in 50 ml of chloroform, the solution is washed thrice with 10 ml of n hydrochloric acid solution, each, thrice with 10 ml of n sodium hydrocarbonate solution, each, and then with 10 ml of water, dried over anhydrous sodium sulfate, and finally evaporated. The residue is dissolved in 5 ml of ethyl acetate, and 10 ml of a 5 n hydrochloric acid solution in ethyl acetate are added. After 30 minutes of standing the reaction mixture is diluted with ether, the separated precipitate is filtered off, and dried in vacuo over anhydrous sodium hydroxide. 2.48 g (94%, calculated for BOC-Nle-OPFP) of H-Nle-Pro-NH₂.HCl are obtained; $R_f^4 = 0.20$.

Step 2: Benzyloxycarbonyl-L-pyroglutamyl-L-norleucyl-L-prolinamide 1.05 g (4 mmoles) of H-Nle-Pro-NH₂.HCl are dissolved in 10 ml of DMFA, and 0.56 ml (4 mmoles) of triethylamine and 1.89 g (4.4 mmoles) of Z-Glp-OPFP are added to the solution under stirring and cooling with ice. After 5 minutes of stirring further 0.56 ml (4 mmoles) of triethylamine are added to the reaction mixture, the mixture is stirred for additional 20 minutes, and then evaporated to dryness in vacuo. The residue is dissolved in 40 ml of chloroform, the solution is shaken twice with 10 ml of n hydrochloric acid, each, thrice with 10 ml of n sodium hydrocarbonate solution, each, and then with 10 ml of water, dried over anhydrous sodium sulfate, and evaporated in vacuo. The oily residue is covered with ether and is allowed to crystallize. 1.52 g of a crude product are obtained, which is recrystallized from 8 ml of ethyl acetate. Thus 1.36 g (72%) of Z-Glp-Nle-Pro-NH$_2$ are obtained; m.p.: 146°–148° C., R$_f^3$=0.32, $[\alpha]_D^{25}$=−79.8° (c=1%, in acetic acid).

Analysis: calculated for C$_{24}$H$_{32}$O$_6$N$_4$ (mol. wt.: 472.55): C: 61.00%, H: 6.83%, N: 11.86 %; found: C: 60.90%, H: 7.04%, N: 11.87%.

Step 3: L-Pyroglutamyl-L-norleucyl-L-prolinamide 1.16 g (2.46 mmoles) of Z-Glp-Nle-Pro-NH$_2$ are dissolved in 25 ml of methanol. 0.2 g of a 10% palladium-on-carbon catalyst is added to the solution, and hydrogen is bubbled through the mixture for 30 minutes. The catalyst is filtered off, the filtrate is evaporated, and the solid, amorphous residue is triturated with ether. The resulting 0.72 g of crude product is dissolved in water, the solution is decolourized, filtered, and the clear filtrate is freeze-dried. 0.66 g (79.5%) of Glp-Nle-Pro-NH$_2$ are obtained: R$_f^4$=0.43, $[\alpha]_D^{25}$=−77.1° (c=1%, in acetic acid). Amino acid analysis: Glu: 0.96 (1.0), Nle: 1.00 (1.0), Pro: 1.00 (1.0).

EXAMPLE 2

L-Pyroglutamyl-L-norvalyl-L-prolinamide

Step 1: L-Norvalyl-L-prolinamide hydrochloride 2.28 g (20 mmoles) of H-Pro-NH$_2$ and 3.83 g (10 mmoles) of BOC-Nva-OPFP (L. Kisfaludy et al.: Hoppe-Seyler's Z. Physiol. Chemie 359, 887 /1978/) are dissolved in 40 ml of DMFA, and after 5 minutes of standing the solution is evaporated in vacuo. The oily residue is dissolved in 50 ml of chloroform, the solution is shaken thrice with 10 ml of n hydrochloric acid, each, thrice with 10 n aqueous sodium hydrocarbonate solution, each, and then with 10 ml of water, dried over anhydrous sodium sulfate, and evaporated. The residue is dissolved in 5 ml of ethyl acetate, and 10 ml of a 5 n hydrochloric acid solution in ethyl acetate are added. After 30 minutes of standing the reaction mixture is diluted with ether, the separated precipitate is filtered off and dried in vacuo over anhydrous sodium hydroxide. 1.83 g (73%, calculated for BOC-Nva-OPFP) of H-Nva-Pro-NH$_2$.HCl are obtained; R$_f^4$=0.10.

Step 2: Benzyloxycarbonyl-L-pyroglutamyl-L-norvalyl-L-prolinamide 1.25 g (5 mmoles) of H-Nva-Pro-NH$_2$.HCl are suspended in 15 ml of DMFA, and 0.7 ml (5 mmoles) of triethylamine and 2.15 g (5 mmoles) of Z-Glp-OPFP are added to the suspension under stirring and cooling with ice. After 5 minutes further 0.7 ml (5 mmoles) of triethylamine are introduced, the mixture is stirred for additional 20 minutes, and then evaporated in vacuo. The residue is dissolved in 50 ml of chloroform, the solution is shaken thrice with 10 ml of n hydrochloric acid, each, thrice with 10 ml of n sodium hydrocarbonate solution, each, and then with 10 ml of water, dried over anhydrous sodium sulfate and then evaporated. The oily residue is covered with ether and allowed to crystallize. The resulting 1.80 g of crude product is recrystallized from a mixture of ethanol and ether to obtain 1.66 g (72%) of Z-Glp-Nva-Pro-NH$_2$; m.p.: 166°–167° C., R$_f^3$=0.29, $[\alpha]_D^{25}$=−87.5° (c=1%, in acetic acid).

Analysis: calculated for C$_{23}$H$_{30}$O$_6$N$_4$ (mol. wt.: 458.52): C: 60.25%, H: 6.59%, N: 12.22%; found: C: 60.08%, H: 6.70%, N: 12.15%.

Step 3: L-Pyroglutamyl-L-norvalyl-L-prolinamide 1.42 g (3.1 mmoles) of Z-Glp-Nva-Pro-NH$_2$ are dissolved in 30 ml of methanol. 0.2 g of a 10% palladium-on-carbon catalyst are added to the solution, and hydrogen is bubbled through the mixture for 30 minutes. The catalyst is filtered off, the filtrate is evaporated, and the amorphous, solid residue is triturated with ether. The resulting crude product is dissolved in water, the solution is decolourized, filtered, and the clear filtrate is freeze-dried. 0.95 g (94%) of Glp-Nva-Pro-NH$_2$ are obtained; R$_f^4$=0.36, $[\alpha]_D^{25}$=−87.0° (c=1%, in acetic acid). Amino acid analysis: Glu: 0.97 (1.0), Nva: 1.09 (1.0), Pro: 1.00 (1.0).

EXAMPLE 3

L-Pyroglutamyl-L-propyl-L-prolinamide

Step 1: L-Propyl-L-prolinamide hydrochloride 2.28 g (20 mmoles) of H-Pro-NH$_2$ and 3.81 g (10 mmoles) of BOC-Pro-OPFP are dissolved in 40 ml of DMFA, and after 5 minutes of standing the solution is evaporated in vacuo. The residue is dissolved in 50 ml of chloroform, the solution is shaken thrice with 10 ml of n hydrochloric acid, each, thrice with 10 ml of n sodium hydrocarbonate solution, each, and then with 10 ml of water, dried over anhydrous sodium sulfate, and then evaporated. The residue is dissolved in 5 ml of ethyl acetate, and 10 ml of a 5 n hydrochloric acid solution in ethyl acetate are added. After 30 minutes of standing the reaction mixture is diluted with ether, the separated precipitate is filtered off and dried in vacuo over anhydrous sodium hydroxide. 2.06 g (83%, calculated for BOC-Pro-OPFP) of H-Pro-Pro-NH$_2$.HCl are obtained; R$_f^4$=0.05.

Step 2: Benzyloxycarbonyl-L-pyroglutamyl-L-prolyl-L-prolinamide 0.75 g (3 mmoles) of H-Pro-Pro-NH$_2$.HCl are suspended in 10 ml of DMFA, and 0.42 ml (3 mmoles) of triethylamine and 1.35 g (3.15 mmoles) of Z-Glp-OPFP are added to the suspension under stirring and cooling with ice. After 5 minutes further 0.42 ml (3 mmoles) of triethylamine are introduced, the mixture is stirred for additional 10 minutes, and the resulting thick suspension is evaporated in vacuo. The crystalline residue is triturated with 8 ml of ethanol and stored at a cold place for 3 hours. Thereafter the precipitate is filtered off to obtain 1.0 g (73%) of Z-Glp-Pro-Pro-NH$_2$; m.p.: 247°–248° C. (decomposition). R$_f^3$=0.19; $[\alpha]_D^{25}$=−82.8° (c=1%, in acetic acid).

Analysis: calculated for C$_{23}$H$_{28}$O$_6$N$_4$ (mol. wt.: 456.50): C: 60.52%, H: 6.18%, N: 12.27%; found: C: 60.03%, H: 6.20%, N: 12.20%.

Step 3: L-Pyroglutamyl-L-prolyl-L-prolinamide 1.0 g (2.2 mmoles) of Z-Glp-Pro-Pro-NH$_2$ is dissolved in 50 ml of acetic acid. 0.2 g of a 10% palladium-on-carbon catalyst are added to the solution, and hydrogen is bubbled through the mixture for one hour. The catalyst is filtered off, the filtrate is evaporated, and the residue is triturated with ether. The resulting 0.60 g of amorphous crude product are dissolved in water, the solution is decolourized, filtered, and the clear filtrate is freeze-dried. 0.50 g (70%) of Glp-Pro-Pro-NH$_2$ are obtained; R$_f^4$=0.10; $[\alpha]_D^{25}$=−223.1° (c=1%, in acetic acid).

EXAMPLE 4

L-Pyroglutamyl-L-valyl-L-prolinamide

Step 1: L-Valyl-L-prolinamide hydrochloride 0.49 g (4.28 mmoles) of H-Pro-$NH_2$ and 0.82 g (2.14 mmoles) of BOC-Val-OPFP are dissolved in 10 ml of DMFA, and after 30 minutes of standing the solution is evaporated in vacuo. The oily residue is dissolved in 10 ml of chlorfrom, the solution is shaken twice with 3 ml of n hydrochloric acid, each, thrice with 3 ml of n sodium hydrocarbonate solution, each, and then with 3 ml of water, dried over anhydrous sodium sulfate, and then evaporated. The residue is dissolved in 3 ml of ethyl acetate, and 3 ml of a 5 n hydrochloric acid solution in ethyl acetate are added. After one hour of standing the reaction mixture is diluted with ether, the separated precipitate is filtered off and dried in vacuo over anhydrous sodium hydroxide. 0.51 g (95%, calculated for BOC-Val-OPFP) of H-Val-Pro-$NH_2$.HCl are obtained; $R_f^4 = 0.10$.

Step 2: Benzyloxycarbonyl-L-pyroglutamyl-L-valyl-L-prolinamide 0.38 g (1.52 mmoles) of H-Val-Pro-$NH_2$.HCl are suspended in 10 ml of DMFA, and 0.22 ml (1.52 mmoles) of triethylamine and 0.69 g (1.6 mmoles) of Z-Glp-OPFP are added to the suspension under stirring and cooling with ice. After 10 minutes further 0.22 ml (1.52 mmoles) of triethylamine are introduced, the mixture is stirred for additional 30 minutes, and then evaporated in vacuo. The residue is dissolved in 15 ml of chloroform, the solution is shaken twice with 5 ml of n hydrochloric acid, each, thrice with 5 ml of sodium hydrocarbonate solution, each, and then with 5 ml of water, dried over anhydrous sodium sulfate, and finally evaporated in vacuo. The oily residue is crystallized from ether to obtain 0.54 g (77%) of Z-Glp-Val-Pro-$NH_2$; m.p.: 116°–118° C., $R_f^3 = 0.30$, $[\alpha]_D^{25} = -100.5°$ (c=1%, in acetic acid).

Analysis: calculated for $C_{23}H_{30}O_6N_4$ (mol. wt.: 458.52): C: 60.25%, H: 6.59%, N: 12.22%; found: C: 59.23%, H: 6.76%, N: 11.71%.

Step 3: L-Pyroglutamyl-L-valyl-L-prolinamide 9.65 g (21.2 mmoles) of Z-Glp-Val-Pro-$NH_2$ are dissolved in 300 ml of water, 2 g of a 10% palladium-on-carbon catalyst are added, and hydrogen is bubbled through the mixture for 5 hours. The catalyst is filtered off, the filtrate is evaporated, the oily residue is dissolved in ethanol, and this solution is also evaporated. This operation is repeated twice more, and then the resulting amorphous, solid residue is triturated with ether. 4.47 g (65%) of Glp-Val-Pro-$NH_2$ are obtained; $R_f^4 = 0.34$, $[\alpha]_D^{25} = -104.9°$ (c=1%, in acetic acid). Amino acid analysis: Glu: 1.03 (1.01), Val: 1.00 (1.0), Pro: 0.94 (1.0).

EXAMPLE 5

L-Pyroglutamyl-L-isoleucyl-L-prolinamide

Step 1: Benzyloxycarbonyl-L-isoleucyl-L-prolinamide 51.4 g (0.1 moles) of Z-Ile-OPFP and 12.5 g (0.11 moles) of H-Pro-$NH_2$ are dissolved in 250 ml of DMFA, and 14.0 ml (0.1 moles) of triethylamine are added to the solution. The reaction mixture is allowed to stand overnight, and then evaporated in vacuo. The oily residue is dissolved in 500 ml of chloroform, the solution is shaken twice with 100 ml of n hydrochloric acid, each, twice with 100 ml of n sodium hydrocarbonate solution, each, and then with 100 ml of water, dried over anhydrous sodium sulfate, and then evaporated. The oily residue is crystallized from a mixture of 100 ml of ether and 100 ml of n-hexane, and the resulting 31.7 g of crude product is recrystallized from a mixture of 60 ml of ethyl acetate and 60 ml of n-hexane. 30.32 g (84%) of Z-Ile-Pro-$NH_2$ are obtained; m.p.: 127°–128° C., $R_f^2 = 0.54$.

Step 2: L-Isoleucyl-L-prolinamide hydrochloride 24.0 g (66.5 mmoles) of Z-Ile-Pro-$NH_2$ are dissolved in 470 ml of methanol, and 30 ml of a 2.4 n hydrochloric acid solution in methanol and 4 g of a 10% palladium-on-carbon catalyst are added to the solution. Hydrogen is bubbled through the mixture for one hour, thereafter the catalyst is filtered off and the filtrate is evaporated. The residue is triturated with ether, and the resulting 20 g of crude product is recrystallized from a mixture of methanol and ether. 16.05 g (81%) of H-Ile-Pro-$NH_2$.HCl are obtained; m.p.: 135°–140° C., $R_f^4 = 0.15$.

Step 3: Benzyloxycarbonyl-L-pyroglutamyl-L-isoleucyl-L-prolinamide 0.90 g (3.5 mmoles) of H-ILe-Pro-$NH_2$.HCl are suspended in 20 ml of DMFA, and 0.49 ml (3.5 mmoles) of triethylamine and 1.57 g (3.7 mmoles) of Z-Glp-OPFP are added to the suspension under stirring and cooling with ice. After 5 minutes further 0.49 ml (3.5 mmoles) of triethylamine are introduced, the mixture is stirred for additional 20 minutes, and then evaporated in vacuo. The residue is dissolved in 30 ml of chloroform, the solution is shaken thrice with 7 ml of n hydrochloric acid, each, thrice with 7 ml of n sodium hydrocarbonate solution, each, and then with 7 ml of water, dried over anhydrous sodium sulfate and finally evaporated. The oily residue is treated several times with ether, the etheral layers are decanted, then it is covered with ether and allowed to crystallize. The resulting crude substance is dissolved in ethyl acetate and precipitated from the solution with ether. 1.18 g (71.5%) of Z-Glp-Ile-Pro-$NH_2$ are obtained; m.p.: 87°–89° C., $R_f^3 = 0.36$, $[\alpha]_D^{25} = -91.4°$ (c=1%, in acetic acid).

Analysis: calculated for $C_{24}H_{32}O_6N_4$ (mol. wt.: 472.55): C: 61.00%, H: 6.83%, N: 11.86%; found: C: 59.19%, H: 6.88%, N: 11.16%.

Step 4: L-Pyroglutamyl-L-isoleucyl-L-prolinamide 4.72 g (10 mmoles) of Z-Glp-Ile-Pro-$NH_2$ are dissolved in 100 ml of methanol, 1 g of a 10% palladium-on-carbon catalyst is added, and hydrogen is bubbled through the mixture for one hour. The catalyst is filtered off, the filtrate is evaporated, and the residue is triturated with ether. The resulting 3.22 g of amorphous crude product are dissolved in water, the solution is decolourized, filtered, and the clear filtrate is freeze-dried. 3.03 g (89%) of Glp-Ile-Pro-$NH_2$ are obtained; $R_f^4 = 0.45$, $[\alpha]_D^{25} = -100.7°$ (c=1%, in acetic acid). Amino acid analysis: Glu: 0.95 (1.0), Ile: 1.00 (1.0), Pro: 1.02 (1.0).

EXAMPLE 6

L-Pyroglutamyl-L-α-aminobutyl-L-prolinamide

Step 1: tert.-Butoxycarbonyl-L-α-aminobutyric acid pentafluorophenyl ester 7.7 g (20 mmoles) of BOC-Abu-OH.DCHA are suspended in 60 ml of ether, and the suspension is shaken with 20 ml of a 2 n sulfuric acid solution until the solid dissolves. The phases are separated from each other, the etheral layer is shaken with 20 ml of 2 n sulfuric acid and 20 ml of water, dried and evaporated. The oily residue, weighing 4.14 g, is dissolved in 25 ml of ethyl acetate together with 3.7 g (20 mmoles) of PFPOH, the solution is cooled to a temperature below 5° C., and 3.92 g (19 mmoles) of DCC are added with stirring. The reaction mixture is stirred for one hour on an ice bath, thereafter the separated DCU is filtered off, the filtrate is evaporated, and the oily residue is dissolved in 50 ml of n-hexane. The solution is stored in a refrigerator for one hour. The separated DCU is filtered off, and the filtrate is concentrated to a final volume of 20 ml, whereupon crystals start to separate. The suspension is allowed to stand at a cold place overnight, and the separated crystals are filtered off. 5.57 g (76%) of BOC-Abu-OPFP are obtained; m.p.: 83°–84° C., $R_f^1=0.86$, $[\alpha]_D^{25}=-32.8°$ (c=1%, in ethyl acetate).

Analysis: calculated for $C_{15}H_{16}O_4NF_5$ (mol. wt.: 369.29):

C: 48.79%, H: 4.37%, N: 3.79%, F: 25.72%; found: C: 48.55%, H: 4.28%, N: 3.70%, F: 25.44%.

Step 2: L-α-Aminobutyryl-L-prolinamide hydrochloride 3.2 g (28 mmoles) of H-Pro-NH$_2$ and 5.16 g (14 mmoles) of BOC-Abu-OPFP are dissolved in 60 ml of DMFA, and after 5 minutes of standing the solution is evaporated in vacuo. The oily residue is dissolved in 100 ml of chloroform, the solution is shaken twice with 20 ml of n hydrochloric acid, each, and then twice with 20 ml of n sodium hydrocarbonate solution, each, dried over anhydrous sodium sulfate, and then evaporated. The oily residue is dissolved in 20 ml of ethyl acetate, and 20 ml of a 6 n hydrochloric acid solution in ethyl acetate are added. After one hour of standing the reaction mixture is diluted with ether, the separated precipitate is filtered off and dried in vacuo over anhydrous sodium hydroxide. The resulting 3.86 g of crude product is triturated with 20 ml of cold DMFA to obtain 2.40 g (73%, calculated for BOC-Abu-OPFP) of H-Abu-Pro-NH$_2$.HCl; $R_f^4=0.10$.

Step 3: Benzyloxycarbonyl-L-pyroglutamyl-L-α-aminobutyryl-L-prolinamide 2.13 g (9 mmoles) of H-Abu-Pro-NH$_2$.HCl are suspended in 30 ml of DMFA, and 1.26 ml (9 mmoles) of triethylamine and 3.95 g (9.2 mmoles) of Z-Glp-OPFP are added to the suspension under stirring and cooling with ice. After 5 minutes further 1.26 ml (9 mmoles) of triethylamine are introduced, the mixture is stirred for additional 20 minutes, and then evaporated in vacuo. The crystalline residue is triturated with 20 ml of ethanol, allowed to stand at a cold place overnight, and then the crystals are filtered off. 3.30 g (82%) of Z-Glp-Abu-Pro-NH$_2$ are obtained; m.p.: 175°–176° C., $R_f^3=0.28$, $[\alpha]_D^{25}=-99.6°$ (c=1%, in acetic acid).

Step 4: L-Pyroglutamyl-L-α-aminobutyryl-L-prolinamide 2.67 g (6 mmoles) of Z-Glp-Abu-Pro-NH$_2$ are dissolved in 100 ml of acetic acid. 0.5 g of a 10% palladium-on-carbon catalyst are added to the solution, and hydrogen is bubbled through the mixture for one hour. The catalyst is filtered off, the filtrate is evaporated, and the residue is triturated with ether. The resulting 1.82 g of amorphous crude product are dissolved in water, the solution is decolourized, filtered, and the clear filtrate is freeze-dried. 1.70 g (91%) of Glp-Abu-Pro-NH$_2$ are obtained; $R_f^4=0.24$, $[\alpha]_D^{25}=-102.5°$ (c=1%, in acetic acid).

EXAMPLE 7

L-Pyroglutamyl-L-α-aminodecanoyl-L-prolinamide

Step 1: L-α-Aminodecanoyl-L-prolinamide hydrochloride 1.37 g (12 mmoles) of H-Pro-NH$_2$ and 2.72 g (6 mmoles) of BOC-Ada-OPFP are dissolved in 20 ml of DMFA, and after 5 minutes of standing the solution is evaporated in vacuo. The oily residue is dissolved in 50 ml of chloroform, the solution is shaken thrice with 10 ml of n hydrochloric acid, each, thrice with 20 ml of n sodium hydrocarbonate solution, each, and then twice with 10 ml of water, each, dried over anhydrous sodium sulfate, and evaporated. The oily residue is dissolved in 3 ml of ethyl acetate, and 5 ml of a 6 n hydrochloric acid solution in ethyl acetate are added. Afte one hour of standing the reaction mixture is diluted with ether, the precipitate is filtered off and dried in vacuo over anhydrous sodium hydroxide. 1.75 g (91%, calculated for BOC-Ada-OPFP) of H-Ada-Pro-NH$_2$.HCl are obtained; $R_f^3=0.11$.

Step 2: Benzyloxycarbonyl-L-pyroglutamyl-L-α-aminodecanoyl-L-prolinamide 1.75 g (5.5 mmoles) of H-Ada-Pro-NH$_2$.HCl and 2.58 g (6 mmoles) of Z-Glp-OPFP are dissolved in 30 ml of DMFA, and 0.77 ml (5.5 mmoles) of triethylamine are added to the solution. After 5 minutes further 0.77 ml (5.5 mmoles) of triethylamine are introduced, the mixture is stirred for additional 20 minutes, and then evaporated in vacuo. The residue is dissolved in 50 ml of chloroform, the solution is shaken thrice with 20 ml of n hydrochloric acid, each, thrice with 20 ml of n sodium hydrocarbonate solution, each, and then twice with 20 ml of water, each, dried over anhydrous sodium sulfate and then evaporated. The foamed oily residue is triturated with ether, the resulting gelly suspension is stored in a refrigerator for 1–2 hours, and then the precipitate is filtered off. The resulting 2.61 g of crude product are recrystallized from 20 ml of ethyl acetate to obtain 2.45 g (84%) of Z-Glp-Ada-Pro-NH$_2$; m.p.: 103°–105° C., $R_f^2=0.19$, $[\alpha]_D^{25}=-63.7°$ (c=1%, in acetic acid).

Analysis: calculated for $C_{28}H_{40}O_6N_4$ (mol. wt.: 528.65): C: 63.62%, H: 7.63%, N: 10.60%; found: C: 63.24%, H: 7.81%; N: 10.57%.

Step 3: L-Pyroglutamyl-L-α-aminodecanoyl-L-prolinamide 1.9 g (3.6 mmoles) of Z-Glp-Ada-Pro-NH$_2$ are dissolved in 40 ml of acetic acid, 0.2 g of a 10% palladium-on-carbon catalyst are added, and hydrogen is bubbled through the mixture for 1.5 hours. The catalyst is filtered off, the filtrate is evaporated, the residue is dissolved in water, the solution is decolourized, filtered and then evaporated. The oily residue is dissolved in 30 ml of chloroform, the solution is dried over anhydrous sodium sulfate, evaporated, and the form-like amorphous solid residue is triturated with ether. 1.20 g (85%) of Glp-Ada-Pro-NH$_2$ are obtained; $R_f^4=0.55$, $[\alpha]_D^{25}=-66.2°$ (c=1%, in acetic acid).

EXAMPLE 8

L-Pyroglutamyl-L-cyclohexylalanyl-L-prolinamide

Step 1: tert.-Butoxycarbonyl-L-cyclohexylalanine pentafluorophenyl ester 9.04 g (20 mmoles) of BOC-Cha-OH.DCHA are suspended in 80 ml of ether, and the suspension is shaken with 20 ml of 2 n sulfuric acid until dissolution occurs. The phases are separated from each other, the etheral layer is washed with 20 ml of 2 n sulfuric acid and 20 ml of water, dried and then evaporated. The resulting 5.7 g of oily substance are dissolved in 30 ml of ethyl acetate together with 3.7 g (20 mmoles) of PFPOH, the solution is cooled to a temperature below 5° C., and 4.12 g (20 mmoles) of DCC are added. The reaction mixture is stirred for one hour under cooling, the separated DCU is filtered off, and the filtrate is evaporated. The oily residue is dissolved in 30 ml of n-hexane, the solution is allowed to stand in a refrigerator for one hour, thereafter the separated DCU is filtered off and the filtrate is diluted with 70 ml of n-hexane. The hexane solution is shaken five times with 40 ml of n sodium hydrocarbonate solution, each, and then twice with 40 ml of water, each, dried over anhydrous sodium sulfate and evaporated. The oily residue crystallizes upon standing: 8.48 g (97%) of BOC-Cha-OPFP are obtained; m.p.: 75°–77° C., $R_f^1 = 0.88$.

Analysis: calculated for $C_{20}H_{24}O_4NF_5$ (mol. wt.: 437.41): C: 54.92%, H: 5.53%, N: 3.20%, F: 21.72%; found: C: 54.67%, H: 5.66%, N: 3.11%, F: 21.43%.

Step 2: L-Cyclohexylalanyl-L-prolinamide hydrochloride 2.28 g (20 mmoles) of H-Pro-NH$_2$ and 4.37 g (10 mmoles) of BOC-Cha-OPFP are dissolved in 40 ml of DMFA, and after 5 minutes of standing the solution is evaporated in vacuo. The oily residue is dissolved in 80 ml of chloroform, the solution is shaken thrice with 20 ml of n hydrochloric acid, each, thrice with 20 ml of n sodium hydrocarbonate solution, each, and then with 20 ml of water, dried over anhydrous sodium sulfate and evaporated. The oily residue is dissolved in 8 ml of ethyl acetate, and 10 ml of a 5 n hydrochloric acid solution in ethyl acetate are added. After one hour the reaction mixture is diluted with ether, the separated precipitate is filtered off and dried in vacuo over anhydrous sodium hydroxide. 2.98 g (97%, calculated for BOC-Cha-OPFP) of H-Cha-Pro-NH$_2$.HCl are obtained; $R_f^4 = 0.33$.

Step 3: Benzyloxycarbonyl-L-pyroglutamyl-L-cyclohexylalanyl-L-prolinamide 2.43 g (8 mmoles) of H-Cha-Pro-NH$_2$.HCl and 3.60 g (8.4 mmoles) of Z-Glp-OPFP are dissolved in 25 ml of DMFA, and 1.12 ml (8 mmoles) of triethylamine are added to the solution. After 5 minutes further 1.12 ml (8 mmoles) of triethylamine are introduced, the mixture is stirred for additional 20 minutes, and then evaporated in vacuo. The residue is dissolved in 80 ml of chloroform, the solution is shaken thrice with 20 ml of n hydrochloric acid, each, thrice with 20 ml of n sodium hydrocarbonate solution, each, and then with 20 ml of water, dried over anhydrous sodium sulfate and evaporated. The oily residue is crystallized from ether, and the resulting 3.88 g of crude product are recrystallized from 30 ml of ethyl acetate. 3.32 g (81%) of Z-Glp-Cha-Pro-NH$_2$ are obtained; m.p.: 165°–166° C., $R_f^2 = 0.17$, $[\alpha]_D^{25} = -67.3°$ (c=1%, in acetic acid).

Analysis: calculated for $C_{27}H_{36}O_6N_4$ (mol. wt.: 512.61): C: 63.26%, H: 7.08%, N: 10.93%; found: C: 63.15%, H: 7.04%, N: 10.91%.

Step 4: L-Pyroglutamyl-L-cyclohexylalanyl-L-prolinamide 3.07 g (6 mmoles) of Z-Glp-Cha-Pro-NH$_2$ are dissolved in 60 ml of ethanol, 0.6 g of a 10% palladium-on-carbon catalyst are added, and hydrogen is bubbled through the mixture for 2 hours. The catalyst is filtered off, the filtrate is evaporated, and the residue is triturated with ether. 2.15 g (95%) of Glp-Cha-Pro-NH$_2$ are obtained as an amorphous solid; $R_f^4 = 0.50$, $[\alpha]_D^{25} = -70.9°$ (c=1%, in acetic acid).

EXAMPLE 9

L-Pyroglutamyl-L-threonyl-L-prolinamide

Step 1: O-Benzyl-L-threonyl-L-prolinamide hydrochloride 1.43 g (12.5 mmoles) of H-Pro-NH$_2$ and 2.98 g (6.27 mmoles) of BOC-Thr(Bzl)-OPFP are dissolved in 20 ml of DMFA, and after 5 minutes of standing the solution is evaporated in vacuo. The oily residue is dissolved in 30 ml of chloroform, the solution is shaken twice with 10 ml of n hydrochloric acid, each, thrice with 10 ml of n sodium hydrocarbonate solution, each, dried over anhydrous sodium sulfate and evaporated. The oily residue is dissolved in 4 ml of ethyl acetate and 5 ml of a 5 n hydrochloric acid solution in ethyl acetate are added. After one hour of standing the reaction mixture is diluted with ether, the separated precipitate is filtered off and dried in vacuo over anhydrous sodium hydroxide. 2.05 g (95%) of H-Thr(Bzl)-Pro-NH$_2$.HCl are obtained as a hydroscopic substance; $R_f^4 = 0.40$.

Step 2: Benzyloxycarbonyl-L-pyroglutamyl-L-O-benzylthreonyl-L-prolinamide 2.05 g (6 mmoles) of H-Thr(Bzl)-Pro-NH$_2$.HCl and 2.69 g (6.27 mmoles) of Z-Glp-OPFP are dissolved in 20 ml of DMFA, and 0.84 ml (6 mmoles) of triethylamine are added dropwise to the solution. After 5 minutes further 0.84 ml of triethylamine are introduced, the mixture is stirred for additional 20 minutes, and then evaporated in vacuo. The residue is dissolved in 50 ml of chloroform, the solution is shaken twice with 10 ml of n hydrochloric acid solution, each, and then thrice with 10 ml of n sodium hydrocarbonate solution, each, dried over anhydrous sodium sulfate and then evaporated. The oily residue is covered with ether and is allowed to crystallize at a cold place. The resulting 2.76 g of amorphous, solid crude product are dissolved in ethyl acetate, the solution is decolourized, evaporated, and the foam-like solid residue is triturated with ether. 2.47 g (75%) of Z-Glp-Thr(Bzl)-Pro-NH$_2$ are obtained.

Step 3: L-Pyroglutamyl-L-threonyl-L-prolinamide 2.04 g (3.7 mmoles) of Z-Glp-Thr(Bzl)-Pro-NH$_2$ are dissolved in 40 ml of acetic acid, 0.4 g of a 10% palladium-on-carbon catalyst are added, and hydrogen is bubbled through the mixture for 4 hours. The catalyst is filtered off, the filtrate is evaporated, and the residue is triturated with ether. The resulting 1.31 g of amorphous crude product are applied onto the top of a column filled with 30 g of silica gel (particle size: 0.063–0.2 mm), and the column is eluted with solvent mixture (3). The main fractions which contain the pure substance are combined, evaporated, and the product is isolated with ether. 0.72 g (59.5%) of Glp-Thr-Pro-NH$_2$ are obtained; $R_f^4 = 0.16$, $[\alpha]_D^{25} = -90.0°$ (c=1%, in acetic acid). Amino acid analysis: Glu: 1.00 (1.0), Thr: 0.99 (1.0), Pro: 1.03 (1.0).

EXAMPLE 10

L-Pyroglutamyl-O-tert.-butyl-L-seryl-L-prolinamide

Step 1: O-tert.-Butyl-L-seryl-L-prolinamide hemioxalate 8.0 g (70 mmoles) of H-Pro-NH$_2$ and 16.0 (34.7 mmoles) of Z-Ser($^t$Bu)-OPFP are dissolved in 120 ml of DMFA, and after 5 minutes of standing the solution is evaporated in vacuo. The oily residue is dissolved in 300 ml of chloroform, the solution is shaken thrice with 80 ml of n hydrochloric acid, each, thrice with 80 ml of n sodium hydrocarbonate solution, each, and then with 80 ml of water, dried over anhydrous sodium sulfate and evaporated. The resulting 18 g of oily substance are dissolved in 300 ml of methanol together with 4.37 g (34.7 mmoles) of oxalic acid dihydrate, 3 g of a 10% palladium-on-carbon catalyst are added, and hydrogen is bubbled through the mixture for one hour. The catalyst is filtered off, the filtrate is evaporated, the residue is triturated with ethyl acetate and then dried in vacuo. 10.8 g (90%, calculated for Z-Ser/$^t$Bu/-OPFP) of H-Ser($^t$Bu)-Pro-NH$_2$.(COOH)$_2$ are obtained as an amorphous, hygroscopic substance: $R_f^4 = 0.22$.

Step 2: Benzyloxycarbonyl-L-pyroglutamyl-O-tert.-butyl-L-seryl-L-prolinamide 6.43 g (18.5 mmoles) of H-Ser($^t$Bu)-Pro-NH$_2$.(COOH)$_2$ and 7.95 g (18.5 mmoles) of Z-Glp-OPFP are dissolved in 80 ml of DMFA, and 5.18 ml (37 mmoles) of triethylamine are added to the solution. After 5 minutes the reaction mixture is evaporated in vacuo and the crystalline residue is triturated with ether. The resulting 9.53 g of crude product are recrystallized from 120 ml of methanol to obtain 7.70 g (83%) of Z-Glp-Ser($^t$Bu)-Pro-NH$_2$; m.p.: 226°–229° C., $R_f^3 = 0.40$, $[\alpha]_D^{25} = 71.6°$ (c=1%, in acetic acid).

Analysis: calculated for $C_{25}H_{34}O_7N_4$ (mol. wt.: 502.57): C: 59.75%, H: 6.82%, N: 11.15%; found: C: 59.55%, H: 6.95%, N: 11.09%.

Step 3: L-Pyroglutamyl-O-tert.butyl-L-seryl-L-prolinamide 4.02 g (8 mmoles) of Z-Glp-Ser($^t$Bu)-Pro-NH$_2$ are dissolved in 160 ml of methanol, 0.8 g of a 10% palladium-on-carbon catalyst are added, and hydrogen is bubbled through the mixture for 30 minutes. The catalyst is filtered off, the filtrate is evaporated, and the residue is covered with ether and allowed to crystallize. The crystals are filtered off to obtain 2.50 g (85%) of Glp-Ser($^t$Bu)-Pro-NH$_2$; m.p.: 186°–187° C., $R_f^4 = 0.45$, $[\alpha]_D^{25} = -60.8°$ (c=1%, in acetic acid). Amino acid analysis: Glu: 1.03 (1.0), Ser: 1.00 (1.0), Pro: 1.00 (1.0).

Analysis: calculated for $C_{17}H_{28}O_5N_4$ (mol. wt.: 368.44): C: 55.42%, H: 7.66%, N: 15.21%; found: C: 55.07%, H: 7.61%, N: 14.94%.

EXAMPLE 11

L-Pyroglutamyl-D-leucyl-L-prolinamide

Step 1: tert.-Butoxycarbonyl-D-leucine pentafluorophenyl ester 4.62 g (20 mmoles) of BOC-D-Leu-OH and 4.23 g (22 mmoles) of PFPOH are dissolved in 50 ml of ethyl acetate, and 4.12 g (20 mmoles) of DCC are added to the solution under stirring and cooling with ice. The reaction mixture is stirred for one hour on an ice bath, thereafter the separated DCU is filtered off and the filtrate is evaporated. The oily residue is dissolved in 100 ml of n-hexane, and the solution is allowed to stand in a refrigerator for one hour. The separated DCU is filtered off, the filtrate is shaken five times with 50 ml of n sodium hydrocarbonate solution and then twice with 50 ml of water, each, dried over anhydrous sodium sulfate and evaporated. The oily residue crystallizes upon standing overnight. 7.0 g (88%) of BOC-D-Leu-OPFP are obtained; m.p.: 53°–55° C., $R_f^1 = 0.88$, $[\alpha]_D^{25} = +31.7°$ (c=1%, in ethyl acetate).

Analysis: calculated for $C_{17}H_{20}NF_5O_4$ (mol.wt.: 397.35): C: 51.39%, H: 5.07%, N: 3.53%, F: 23.91%; found: C: 51.51%, H: 4.68%, N: 3.66%, F: 23.65%.

Step 2: D-Leucyl-L-prolinamide hydrochloride 3.42 g (30 mmoles) of H-Pro-NH$_2$ and 60.0 g (15 mmoles) of BOC-D-Leu-OPFP are dissolved in 60 ml of DMFA, and after 5 minutes of standing the solution is evaporated in vacuo. The residue is dissolved in 100 ml of chloroform, the solution is shaken twice with 20 ml of n hydrochloric acid, each, thrice with 20 ml of n sodium hydrocarbonate solution, each, and then with 20 ml of water, dried over anhydrous sodium sulfate and evaporated. The oily residue is dissolved in 10 ml of ethyl acetate and 15 ml of a 4 n hydrochloric acid solution in ethyl acetate are added. After one hour of standing the reaction mixture is diluted with ether, the separated precipitate is filtered off and dried in vacuo over anhydrous sodium hydroxide. 3.66 g (92.5%, calculated for BOC-D-Leu-OPFP) of H-D-Leu-Pro-NH$_2$.HCl are obtained; $R_f^4 = 0.26$.

Step 3: Benzyloxycarbonyl-L-pyroglutamyl-D-leucyl-L-prolinamide 3.66 g (13.9 mmoles) of H-D-Leu-Pro-NH$_2$.HCl and 6.43 g (15 mmoles) of Z-Glp-OPFP are dissolved in 50 ml of DMFA, and 1.95 ml (13.9 mmoles) of triethylamine are added to the solution under stirring and cooling with ice. After 5 minutes of stirring further 1.95 ml (13.9 mmoles) of triethylamine are introduced, the mixture is stirred for additional 20 minutes and then evaporated in vacuo. The residue is dissolved in 120 ml of chloroform, the solution is shaken thrice with 30 ml of n hydrochloric acid, each, thrice with 30 ml of n sodium hydrocarbonate solution, each, and then with 30 ml of water, dried over anhydrous sodium sulfate and evaporated. The oily residue is crystallized from ether, and the resulting 6 g of crude product are recrystallized from 30 ml of ethanol. 5.48 g (77%) of Z-Glp-D-Leu-Pro-NH$_2$ are obtained; m.p.: 189°–194° C., $R_f^3 = 0.48$, $[\alpha]_D^{25} = -33.2°$ (c=1%, in acetic acid).

Step 4: L-Pyroglutamyl-D-leucyl-L-prolinamide 3.78 g (8 mmoles) of Z-Glp-D-Leu-Pro-NH$_2$ are dissolved in 150 ml of methanol, 0.8 g of a 10% palladium-on-carbon catalyst are added, and hydrogen is bubbled through the mixture for one hour. The catalyst is filtered off, the filtrate is evaporated, and the residue is triturated with ether. The resulting 2.5 g of amorphous crude product are dissolved in water, the solution is decolourised, filtered, and the clear filtrate is freeze-dried. 2.35 g (87%) of Glp-D-Leu-Pro-NH$_2$ are obtained; $R_f^4 = 0.48$, $[\alpha]_D^{25} = -83.3°$ (c=1%, in acetic acid).

EXAMPLE 12

L-Pyroglutamyl-L-leucyl-L-proline ethylamide

Step 1: L-Leucyl-L-proline ethylamide hydrochloride 1.67 g (7.2 mmoles) of H-Pro-NH-Et.(COOH)$_2$ are suspended in 20 ml of ethyl acetate, and 2.0 ml (14.4 mmoles) of triethylamine and 2.38 g (6 mmoles) of BOC-Leu-OPFP are added to the suspension. After 5 minutes the reaction mixture is shaken twice with 5 ml of n hydrochloric acid, each, thrice with 5 ml of n sodium hydrocarbonate solution, each, and then with 5 ml of water, dried over anhydrous sodium sulfate and evaporated. The oily residue is treated with 10 ml of a 5 n hydrochloric acid solution in ethyl acetate for 20 minutes, thereafter the mixture is diluted with ether. The separated precipitate is filtered off and dried in vacuo over anhydrous sodium hydroxide. 1.46 g (83%, calculated for BOC-Leu-OPFP) of H-Leu-Pro-NH- Et.HCl are obtained as a hygroscopic substance; $R_f^4 = 0.43$.

Step 2: Benzyloxycarbonyl-L-pyroglutamyl-L-leucyl-L-proline ethylamide 1.17 g (4 mmoles) of H-Leu-Pro-NH-Et.HCl and 1.72 g (4 mmoles) of Z-Glp-OPFP are dissolved in 15 ml of DMFA, and 0.56 ml (4 mmoles) of triethylamine are added to the solution. After 5 minutes further 0.56 ml (4 mmoles) of triethylamine are introduced, and the reaction mixture is evaporated in vacuo. The oily residue is dissolved in 40 ml of chloroform, the solution is shaken twice with 10 ml of n hydrochloric acid, each, thrice with 10 ml of n sodium hydrocarbonate solution, each, and then with 10 ml of water, dried over anhydrous sodium sulfate and evaporated. The residue is triturated with n-hexane to obtain 1.61 g (80.5%) of Z-Glp-Leu-Pro-NH-Et as an amorphous substance; $R_f^3 = 0.50$, $[\alpha]_D^{25} = -89.0°$ (c=1%, in acetic acid).

Step 3: L-Pyroglutamyl-L-leucyl-L-proline ethylamide 1.07 g (2.14 mmoles) of Z-Glp-Leu-Pro-NH-Et are dissolved in 30 ml of water, 0.25 g of a 10% palladium-on-carbon catalyst are added, and hydrogen is bubbled through the mixture for 1.5 hours. The catalyst is filtered off, the filtrate is evaporated, and the oily residue is dissolved in 20 ml of chloroform. The solution is dried over anhydrous sodium sulfate and then evaporated. A foam-like solid residue is obtained, which is triturated with a mixture of ether and hexane. 0.52 g (66%) of Glp-Leu-Pro-NH-Et are obtained; $R_f^4 = 0.57$, $[\alpha]_D^{25} = -94.5°$ (c=1%, in acetic acid).

EXAMPLE 13

L-Pyroglutamyl-L-leucyl-L-proline n-decylamide

Step 1: Benzyloxycarbonyl-L-proline n-decylamide 5.0 g (20 mmoles) of Z-Pro-OH are dissolved in 50 ml of DMFA, 2.8 ml (20 mmoles) of triethylamine are added to the solution, and the mixture is cooled to $-10°$ C. The mixture is stirred at the same temperature, 2.8 ml (21.5 mmoles) of isobutyl chloroformate are added dropwise, and after 10 minutes 4.4 ml (22 mmoles) of n-decylamine are introduced dropwise. After the addition the reaction mixture is stirred at 0° C. for 30 minutes and then at room temperature for 2 hours. The resulting suspension is filtered, the filtrate is evaporated, and the residue is dissolved in 100 ml of ethyl acetate. The solution is shaken four times with 50 ml of n hydrochloric acid, each, twice with 50 ml of n sodium hydrocarbonate solution, each, and then with 50 ml of water, dried over anhydrous sodium sulfate and evaporated. The oily residue is crystallized from n-hexane to obtain 5.43 g (70%) of Z-Pro-NH-$C_{10}H_{21}$; m.p.: 78°-80° C., $R_f^2 = 0.75$.

Step 2: L-Proline n-decylamide hemioxalate 5.0 g (12.9 mmoles) of Z-Pro-NH-$C_{10}H_{21}$ and 2.02 g (16 mmoles) of oxalic acid dihydrate are dissolved in 100 ml of methanol, 0.8 g of a 10% palladium-on-carbon catalyst are added, and hydrogen is bubbled through the mixture for 2 hours. The reaction mixture is heated, the catalyst is filtered off, and the filtrate is evaporated. The crystalline residue is triturated with ether and then filtered off to obtain 3.9 g (88%) of H-Pro-NH-$C_{10}H_{21}$.(COOH)$_2$; m.p.: 152°-154° C., $R_f^3 = 0.16$.

Step 3: L-Leucyl-L-proline n-decylamide hydrochloride 3.44 g (10 mmoles) of H-Pro-NH-$C_{10}H_{21}$.(COOH)$_2$ and 2.0 g (5 mmoles) of BOC-Leu-OPFP are dissolved in 30 ml of DMFA, and 2.8 ml (20 mmoles) of triethylamine are added to the solution. After 5 minutes of standing the reaction mixture is evaporated, the oily residue is dissolved in 50 ml of n-hexane, the solution is shaken five times with 30 ml of n hydrochloric acid, each, thrice with 30 ml of n sodium hydrocarbonate solution, each, and then with 30 ml of water, dried over anhydrous sodium sulfate and evaporated. The oily residue is dissolved in 10 ml of a 5 n hydrochloric acid solution in ethyl acetate, the solution is allowed to stand for 30 minutes and then evaporated. The foam-like, amorphous residue is triturated with n-hexane, filtered and dried in vacuo over anhydrous sodium hydroxide. 1.05 g (60%, calculated for BOC-Leu-OPFP) of H-Leu-Pro-NH-$C_{10}H_{21}$.HCl are obtained; $R_f^3 = 0.17$.

Step 4: Benzyloxycarbonyl-L-pyroglutamyl-L-leucyl-L-proline n decylamide 1.03 g (2.55 mmoles) of H-Leu-Pro-NH-$C_{10}H_{21}$.HCl are dissolved in 10 ml of DMFA, and 0.36 ml (2.55 mmoles) of triethylamine and 1.1 g (2.55 mmoles) of Z-Glp-OPFP are added to the solution. After 5 minutes of stirring further 0.36 ml (2.55 mmoles) of triethylamine are introduced, the mixture is stirred for additional 20 minutes and then evaporated in vacuo. The residue is dissolved in 20 ml of chloroform, the solution is shaken five times with 10 ml of n hydrochloric acid, each, thrice with 10 ml of n sodium hydrocarbonate solution, each, and then with 10 ml of water, dried over anhydrous sodium sulfate and evaporated. The oily residue is covered with ether and is allowed to crystallize. 1.22 g (78%) of Z-Glp-Leu-Pro-NH-$C_{10}H_{21}$ are obtained; m.p.: 108°-109° C., $R_f^2 = 0.50$, $[\alpha]_D^{25} = -74.5°$ (c=1%, in acetic acid).

Analysis: calculated for $C_{34}H_{52}O_6N_4$ (mol.wt.: 612.82): C: 66.64%, H: 8.55%, N: 9.14%; found: C:66.43%, H: 8.84%, N: 9.13%.

Step 5: L-Pyroglutamyl-L-leucyl-L-proline n-decylamide 1.22 g (2 mmoles) of Z-Glp-Leu-Pro-NH-$C_{10}H_{21}$ are dissolved in 30 ml of methanol, 0.2 g of a 10% palladium-on-carbon catalyst are added, and hydrogen is bubbled through the mixture for 30 minutes. The catalyst is filtered off, the filtrate is evaporated, and the oily residue is crystallized from n-hexane. The resulting 0.85 g of crude product are recrystallized from 4 ml of ethyl acetate to obtain 0.74 g (77%) of Glp-Leu-Pro-NH-$C_{10}H_{21}$; m.p.: 140°-141° C., $R_f^4 = 0.76$, $[\alpha]_D^{25} = -71.3°$ (c=1%, in acetic acid). Amino acid analysis: Glu: 0.97 (1.0), Leu: 1.00 (1.0), Pro: 1.01 (1.0).

EXAMPLE 14

L-Pyroglutamyl-L-leucyl-L-proline 2-dimethylaminoethylamide

Step 1: tert.-Butoxycarbonyl-L-proline (2-dimethylamino)-ethylamide 11.43 g (30 mmoles) of BOC-Pro-OPFP are dissolved in 100 ml of ether, and 6.54 ml (60 mmoles) of N,N-dimethylaminoethylamine are added to the solution. After 10 minutes of standing the reaction mixture is shaken thrice with 30 ml of water, each, the aqueous solutions are combined, and solid sodium carbonate is added to adjust the pH of the solution to 10. The resulting aqueous alkaline solution is extracted four times with 20 ml of ethyl acetate, each. The ethyl acetate solutions are combined, washed with 20 ml of water, dried over anhydrous sodium sulfate and evaporated. The oily residue crystallizes upon standing. 6.71 g (78.5%) of BOC-Pro-NH-(CH$_2$)$_2$N(CH$_3$)$_2$ are obtained; R$_f^4$=0.29.

Step 2: L-Leucyl-L-proline (2-dimethylamino)ethylamide dihydrochloride 6.71 g (23.5 mmoles) of BOC-Pro-NH-(CH$_2$)$_2$-N(CH$_3$)$_2$ are treated with 30 ml of a 5 n hydrochloric acid solution in ethyl acetate, and after 30 minutes the reaction mixture is evaporated. The oily residue is dissolved in 50 ml of chloroform, and 2.8 ml (20 mmoles) of triethylamine are added. The resulting clear solution is admixed with 6.74 g (17 mmoles) of BOC-Leu-OPFP, and after one hour of stirring further 2.8 ml (20 mmoles) of triethylamine are added dropwise to the mixture. The reaction mixture is allowed to stand overnight, evaporated, and the oily residue is dissolved in 50 ml of water. Solid sodium carbonate is added to the solution to adjust the pH to 10, and the protected dipeptide is extracted with ethyl acetate. The ethyl acetate solution is dried over anhydrous sodium sulfate and then evaporated. The oily residue is admixed with a 5 n solution of hydrochloric acid in ethyl acetate, and after one hour the reaction mixture is evaporated. The residue is triturated with ether, and the resulting amorphous, strongly hygroscopic substance is filtered off and dried in vacuo over anhydrous sodium hydroxide. 4.5 g (12.1 mmoles) of H-Leu-Pro-NH-(CH$_2$)$_2$-N(CH$_3$)$_2$.2HCl are obtained; R$_f^4$=0.05.

Step 3: L-Pyroglutamyl-L-leucyl-L-proline (2-dimethylamino)-ethylamide 2.6 g (7 mmoles) of H-Leu-Pro-NH-(CH$_2$)$_2$-N(CH$_3$)$_2$.2HCl are dissolved in 30 ml of DMFA, and 1.96 ml (14 mmoles) of triethylamine are added to the solution. The separated precipitate is filtered off, and the filtrate is added dropwise, under stirring and ice-cooling, to a solution of 3.29 g (7.7 mmoles) of Z-Glp-OPFP in 10 ml of DMFA. The addition requires 30 minutes. When the addition is complete the reaction mixture is allowed to stand for 4 hours and then evaporated in vacuo. The oily residue is dissolved in 50 ml of water, the solution is acidified to pH 3 with concentrated hydrochloric acid, and the acidic mixture is washed thrice with 20 ml of ethyl acetate, each. The pH of the aqueous phase is adjusted to 10 with solid sodium carbonate, and the resulting solution is extracted five times with 30 ml of ethyl acetate, each. The ethyl acetate solutions are combined, dried over anhydrous sodium sulfate and evaporated. The resulting 3.05 g (5.6 mmoles) of protected tripeptide, obtained as an oily substance, are dissolved in 60 ml of water, 5.6 ml of n hydrochloric acid and 0.6 g of a 10% palladium-on-carbon catalyst are added to the solution, and hydrogen is bubbled through the mixture for 30 minutes. The catalyst is filtered off, the filtrate is evaporated, and the oily residue is partitioned between 50 ml of chloroform and 20 ml of n sodium hydrocarbonate solution. The chloroform phase is separated, dried over anhydrous sodium sulfate, evaporated, and the residue is triturated with n-hexane. The resulting 2.0 g of amorphous crude product are dissolved in water, the solution is decolourized, filtered, and the clear filtrate is freeze-dried. 1.72 g (60%) of Glp-Leu-Pro-NH-(CH$_2$)$_2$-N(CH$_3$)$_2$ are obtained; R$_f^4$=0.06, [α]$_D^{25}$=−71.7° (c=1%, in acetic acid). Amino acid analysis: Glu: 1.02 (1.0), Leu: 1.00 (1.0), Pro: 1.03 (1.0).

EXAMPLE 15

L-Pyroglutamyl-L-histidyl-D-pipecolic acid amide

Step 1: Benzyloxycarbonyl-D-pipecolic acid amide 13.15 g (50 mmoles) of Z-D-Pip-OH (L. Balaspiri et al.: Monatsh. Chem. 101, 177/1970/) are dissolved in 100 ml of ethyl acetate, 7.0 ml (50 mmoles) of triethylamine are added, and the solution is cooled to −20° C. 6.5 ml (50 mmoles) of isobutyl chloroformate are added dropwise to the stirred solution at the same temperature, thereafter the mixture is stirred for 15 minutes, and then gaseous ammonia is introduced into the mixture at −10° C. for 1.5 hours. The separated precipitate is filtered off, the filtrate is washed with n hydrochloric acid, n sodium hydrocarbonate solution and water, dried over anhydrous sodium sulfate and evaporated. The residue is crystallized from a mixture of ethyl acetate and ether to obtain 11.5 g (88%) of Z-D-Pip-NH$_2$; m.p.: 114°–115° C., R$_f^2$=0.50, [α]$_D^{25}$=+32.0° (c=1%, in methanol).

Analysis: calculated for C$_{14}$H$_{18}$O$_3$N$_2$ (mol.wt.: 262.30): N: 10.68%; found: N: 10.63%.

Step 2: D-Pipecolic acid amide 3.93 g (15 mmoles) of Z-D-Pip-NH$_2$ are dissolved in 75 ml of methanol, 0.5 g of a 10% palladium-on-carbon catalyst are added, and hydrogen is bubbled through the mixture for one hour. The catalyst is filtered off, the filtrate is evaporated, and the residue is triturated with ether. 1.70 g (90%) of H-D-Pip-NH$_2$ are obtained: m.p.: 161°–163° C., R$_f^4$=0.10, [α]$_D^{25}$=+31.0° (c=1%, in methanol).

Step 3: Benzyloxycarbonyl-L-glutaminyl-L-histidine hydrazide 71.0 g (0.165 moles) of Z-Gln-His-OMe (H. Kappeler: Helv. Chim. Acta 44, 476/1961/) are dissolved in 700 ml of DMFA, and 33.6 ml (0.495 moles) of hydrazine hydrate are poured into the solution. After 3 days of standing the reaction mixture is diluted with 600 ml of ethyl acetate, allowed to stand at a cold place overnight, and then the separated precipitate is filtered off. The resulting 71.65 g of crude product are recrystallized from 1800 ml of methanol to obtain 55.1 g (78%) of Z-Gln-His-N$_2$H$_3$; m.p.: 198°–200° C., R$_f^4$=0.28.

Analysis: calculated for C$_{19}$H$_{25}$O$_5$N$_7$ (mol.wt.: 431.40): C: 52.90%, H: 5.84%, N: 22.72%; found: C: 52.21%, H: 5.73%, N: 22.78%.

Step 4: Benzyloxycarbonyl-L-glutaminyl-L-histidyl-D-pipecolic acid amide 5.39 g (12.5 mmoles) of Z-Gln-His-N$_2$H$_3$ are suspended in 100 ml of DMFA, and 4.6 ml (37.5 mmoles) of a 8.1 n solution of hydrochloric acid in dioxane are added. The resulting solution is cooled to −20° C., and 1.63 ml (13.7 mmoles) of tert.-butylnitrite are added to the stirred solution dropwise at −15° C. The reaction mixture is stirred at −10° C. for 20 minutes, and then 3.5 ml (25 mmoles) of triethylamine and a solution of 1.57 g (12.5 mmoles) of H-D-Pip-NH$_2$ in 10 ml of DMFA are introduced dropwise at the same temperature. Thereafter additional 1.75 ml (12.5 mmoles) of triethylamine are added dropwise to the mixture. After the addition the mixture is stirred for one additional hour at −10° C. and then allowed to stand at 2° C. overnight. Next day the precipitate is filtered off, the filtrate is evaporated in vacuo, and the amorphous residue is triturated with ethyl acetate. The crude product is applied onto the top of a silica gel column, and the silica gel column is eluted with solvent mixture (2). The fractions which contain the pure product are combined and evaporated, and the residue is triturated with ether. 2.76 g (42%) of Z-Gln-His-D-Pip-NH$_2$ are obtained as an amorphous substance; $R_f^4 = 0.10$.

Step 5: L-Pyroglutamyl-L-histidyl-D-pipecolic acid amide 2.63 g (5 mmoles) of Z-Gln-His-D-Pip-NH$_2$ are dissolved in 50 ml of acetic acid, 0.5 g of a 10% palladium-on-carbon catalyst are added, and hydrogen is bubbled through the mixture for one hour. The catalyst is filtered off, the filtrate is heated to 60°–70° C., maintained at this temperature for 30 minutes, and then evaporated in vacuo. The residue is dissolved in water, the solution is passed through Dowex 2 ion exchange resin in the OH cycle, and then evaporated. The resulting crude product is applied onto the top of a silica gel column, and the column is eluted with solvent mixture (1). The fractions which contain the pure product are combined and evaporated. The residue is dissolved in water, the solution is decolourized, filtered, and the clear filtrate is evaporated. The amorphous residue is dried in vacuo over phosphorous pentoxide. 704 mg (51%) of Glp-His-D-Pip-NH$_2$ are obtained; $R_f^4 = 0.10$; $[\alpha]_D^{25} = +16.0°$ (c=1%, in water). Amino acid analysis: Glu: 1.03 (1.0), His: 1.00 (1.0), Pip: 0.96 (1.0).

EXAMPLE 16

L-Pyroglutamyl-L-histidyl-L-homoprolinamide

Step 1: tert.-Butoxycarbonyl-L-homoprolinamide 2.29 g (10 mmoles) of BOC-HPro-OH are dissolved in 30 ml of ethyl acetate, 1.4 ml (10 mmoles) of triethylamine are added to the solution, and then 1.3 ml (10 mmoles) of isobutyl chloroformate are added dropwise at −10° C. After 15 minutes of stirring gaseous ammonia is passed through the mixture at −10° C. for 0.5 hours, and the resulting mixture is allowed to stand at 0°–5° C. for 2 hours. The separated precipitate is filtered off, the filtrate is evaporated, and the oily residue is dissolved in 30 ml of chloroform. The solution is shaken twice with 10 ml of n hydrochloric acid, each, twice with 10 ml of n sodium hydrocarbonate solution, each, and then with 10 ml of water, dried over anhydrous sodium sulfate and evaporated. The oily residue is crystallized from n-hexane, and the resulting 1.96 g of crude product are recrystallized from a mixture of ethyl acetate and ether. 1.78 g (78%) of BOC-HPro-NH$_2$ are obtained; m.p.: 138°–140° C., $R_f^2 = 0.43$, $[\alpha]_D^{25} = -24.85°$ (c=1%, in acetic acid).

Analysis: calculated for C$_{11}$H$_{20}$O$_3$N$_2$ (mol.wt.: 228.29): C: 57.87%, H: 8.83%, N: 12.27%; found: C: 57.60%, H: 8.89%, N: 12.11%.

Step 2: L-Homoprolinamide hydrochloride 1.6 g (7 mmoles) of BOC-HPro-NH$_2$ are dissolved in 10 ml of ethyl acetate under heating. The solution is cooled to room temperature, and 10 ml of a 6 n hydrochloric acid solution in ethyl acetate are added. After one hour of standing the mixture is diluted with ether, the separated precipitate is triturated and then filtered off. 1.05 g (91%) of H-HPro-NH$_2$.HCl are obtained; m.p.: 178°–180° C., $R_f^6 = 0.32$, $[\alpha]_D^{25} = +26.2°$ (c=1%, in methanol).

Step 3: Benzyloxycarbonyl-L-glutaminyl-L-histidyl-L-homoprolinamide 5.39 g (12.5 mmoles) of Z-Gln-His-N$_2$H$_3$ are suspended in 100 ml of DMFA, and 4.6 ml (37.5 mmoles) of a 8.1 n solution of hydrochloric acid in dioxane are added. The resulting solution is cooled to −20° C., and 1.63 ml (13.7 mmoles) of tert.-butylnitrite are added to the solution dropwise under stirring at −15° C. Thereafter the mixture is stirred at −10° C. for 20 minutes and 3.5 ml (25 mmoles) of triethylamine are added.

2.07 g (12.5 mmoles) of H-Hpro-NH$_2$.HCl are dissolved in 10 ml of DMFA, and 1.75 ml (12.5 mmoles) of triethylamine are added to the solution. The separated precipitate is filtered off, and the filtrate is added dropwise to the above azide solution at −10° C. Thereafter 1.75 ml (12.5 mmoles) of triethylamine are added to the mixture. The resulting mixture is stirred at −10° C. for one additional hour, and then allowed to stand at 2° C. overnight. Next day the separated precipitate is filtered off, the filtrate is evaporated in vacuo, and the amorphous residue is triturated with ethyl acetate. The crude product is applied onto the top of a silica gel column, and the column is eluted with solvent mixture (2). The fractions which contain the pure product are combined and evaporated, and the residue is triturated with ether to obtain 2.35 g (36%) of Z-Gln-His-HPro-NH$_2$; $R_f^4 = 0.30$.

Step 4: L-Pyroglutamyl-L-histidyl-L-homoprolinamide 2.1 g (4 mmoles) of Z-Gln-His-HPro-NH$_2$ are dissolved in 40 ml of acetic acid, 0.4 g of a 10% palladium-on-carbon catalyst are added, and hydrogen is bubbled through the mixture for one hour. The catalyst is filtered off, the filtrate is heated to 60°–70° C., maintained at this temperature for 30 minutes, and then evaporated in vacuo. The resulting crude product is subjected to ion exchange and purified as described in Step 5 of Example 15. 618 mg (56%) of Glp-His-HPro-NH$_2$ are obtained; $R_f^4 = 0.08$, $[\alpha]_D^{25} = -24.0°$ (c=1%, in methanol). Amino acid analysis: Glu: 0.97 (1.0), His: 1.00 (1.0), HPro: 0.91 (1.0).

What we claim is:

1. A peptide derivative of the general formula Glp-X-Y-NH-A, wherein

X is L-norleucyl, L-leucyl, D-leucyl, L-isoleucyl, L-norvalyl, L-valyl, L-prolyl, L-threonyl, L-2-aminobutyryl, L-2-aminodecanoyl, L-cyclohexylalanyl, O-tert.-butyl-L-seryl or L-histidyl group, Y is a L-prolyl, L-homoprolyl or D-pipecolyl group, and A is hydrogen, alkyl of 1 to 10 carbon atoms or alkyl of 1 to 3 carbon atoms substituted with a dimethylamino group, with the proviso that when X is L-histidyl, then Y is not L-prolyl, when X is L-norleucyl, L-leucyl, D-leucyl, L-norvalyl, L-valyl, L-prolyl, L-threonyl, L-2-aminobutyryl, L-2-aminodecanoyl, L-cyclohexylalanyl or O-tert.-butyl-L-seryl, then Y is not L-homoprolyl or D-pipecolyl and when X is L-leucyl, D-leucyl, L-norleucyl, L-isoleucyl, L-norvalyl or L-valyl, then A is not hydrogen, or a pharmaceutically acceptable salt or complex thereof.

2. L-Pyroglutamyl-L-prolyl-L-prolinamide.

3. L-Pyroglutamyl-L-leucyl-L-proline ethylamide.

4. L-Pyroglutamyl-L-α-aminobutyryl-L-prolinamide.

5. A pharmaceutical composition for use in (a) decreasing the duration of sleeping caused by barbituates and alcohol and/or (b) suppressing hypothermy provoked by various drugs and/or (c) increasing locomotive activity and/or (d) inhibiting catalepsy provoked by Haloperidol comprising an effective amount of an active ingredient comprising at least one compound of the formula Glp-X-Y-NH-A, wherein X is L-norleucyl, L-leucyl, D-leucyl, L-isoleucyl, L-norvalyl, L-valyl, L-prolyl, L-threonyl, 2-aminobutyryl, L-2-aminodecanoyl, L-cyclohexylalanyl, O-tert.-butyl-L-seryl or L-histidyl, Y is L-prolyl, L-homoprolyl or D-pipecolyl, and A is hydrogen, alkyl of 1 to 10 carbon atoms or alkyl of 1 to 3 carbon atoms having a dimethylamino substituent, with the proviso that when X is L-histidyl, then Y is not L-prolyl, when X is L-leucyl, then A is not hydrogen and when X is L-norleucyl, L-leucyl, D-leucyl, L-norvalyl, L-valyl, L-prolyl, L-threonyl, L-isoleucyl, L-2-aminobutyryl, L-2-aminodecanoyl, L-cyclohexylalanyl, or L-tert.-butyl-seryl, Y is not L-homoprolyl or D-pipecolyl, or a pharmaceutically acceptable salt or complex thereof and a pharmaceutical carrier or diluent.

* * * * *